United States Patent [19]

Nagano et al.

[11] Patent Number: 4,815,832

[45] Date of Patent: Mar. 28, 1989

[54] TILTING DEVICE FOR SURGICAL MICROSCOPES

[75] Inventors: Takashi Nagano, Hachiouji; Takashi Fukaya, Ina, both of Japan

[73] Assignee: Olympus Optical Co., Ltd., Tokyo, Japan

[21] Appl. No.: 87,831

[22] Filed: Aug. 21, 1987

[30] Foreign Application Priority Data

Aug. 23, 1986 [JP] Japan .................. 61-197678

[51] Int. Cl.⁴ .................. G02B 23/16; F16L 3/00
[52] U.S. Cl. .................. 350/522; 248/123.1
[58] Field of Search .................. 350/522, 521; 248/123.1, 280.1

[56] References Cited

U.S. PATENT DOCUMENTS

| | | | |
|---|---|---|---|
| 3,762,796 | 10/1987 | Heller | 350/522 |
| 3,762,797 | 10/1973 | Heller | 350/522 |
| 3,887,267 | 6/1975 | Heller | 350/522 |
| 3,891,301 | 6/1975 | Heller | 350/522 |
| 4,339,100 | 7/1982 | Heller et al. | 248/123.1 |
| 4,344,595 | 8/1982 | Heller et al. | 248/123.1 |
| 4,364,535 | 12/1982 | Itoh et al. | 350/522 |
| 4,383,455 | 5/1983 | Tuda et al. | 248/123.1 |
| 4,500,251 | 2/1985 | Kiryu et al. | 248/123.1 |
| 4,515,333 | 5/1985 | Pugh et al. | 248/123.1 |
| 4,741,607 | 5/1988 | Heller | 350/522 |

FOREIGN PATENT DOCUMENTS

| | | | |
|---|---|---|---|
| 202399 | 2/1986 | European Pat. Off. | 248/123.1 |
| 3444313 | 8/1985 | Fed. Rep. of Germany | 350/522 |
| 935256 | 7/1988 | France | 350/522 |

*Primary Examiner*—Jon W. Henry
*Attorney, Agent, or Firm*—Cushman, Darby & Cushman

[57] ABSTRACT

A tilting device for surgical microscopes comprising: a supporting apparatus composed of a parallelogram link mounted to be movable three-dimensionally on a frame through a mounting member; and a spring connected between another end portion distant from one end portion of a supporting member to support a microscope and the mounting member, in which rotation moment caused by the weight of the microscope with rotation of the center of gravity of the microscope attached to one end portion of the supporting apparatus is adapted to be offset by reverse rotation moment relying on the elasticity of the spring, in order to make it possible to secure a wide working space for operations in spite of a small size, simplify the structure, reduce the cost of manufacture, and perform smooth operation in the best balance.

13 Claims, 6 Drawing Sheets

TILTING DEVICE FOR SURGICAL MICROSCOPES

BACKGROUND OF THE INVENTION (a) Field of the Invention

The present invention relates to a tilting device to be provided on a frame, stand or the like holding a surgical microscope.

(b) Description of the Prior Art

Recently, with a considerable progress of medicine, a new remarkable operation and its manipulation technique have been developed and, also in the field of microsurgery in which a microsurgical operation is performed while being observed through a microscope for enlargement, the demand for surgical microscopes with a higher degree of performance has been increased with the progress mentioned above.

In surgical operations on cerebral in particular, it is strongly demanded to position smoothly and easily the surgical microscope and therefore time necessary for the changes of an observation angle which will often be performed during the operations needs to be shortened as far as possible. That is, the surgical microscope has to be supported to a stand or a ceiling suspension holder so that it can be moved rapidly and accurately into a desired position within a working space and fixed at the desired position, without any obstruction to the operation.

Further, it is often seen of late that a photographing devce is attached to the microscope to record various symptoms of patient and a TV camera is mounted on the microscope for the education of surgeons and nurses. As a result, the surgical microscope increases in weight and requires an arm and base to compensate the weight, holding the operability mentioned above.

In order to satisfy these requirements, for example, U.S. Pat. Nos. 3,762,796 and 3,762,797 disclose a position adjustable stand device comprising a link mechanism held to a fixed support through a three-axis full Cardan link mechanism allowing its freely combined rotational movement about three axes perpendicular to each other by means of a handgrip to attach anoptical observation instrument to the member at the end portion of the link mechanism capable of freely changing an angular position within a three-dimensional space. With the three axis full Cardan link mechanism used in this device, however, it is essential that the microscope is supported in such a way that the optical observation instrument or microscope (preferably its center of gravity) lies at the intersection of the three rotational axes perpendicular to each other. For this reason, not only each arm constructing the three-axis full Cardan link mechanism becomes complicated in shape and expensive, but also the entire stand device becomes large-sized due to the arrangement of the Cardan arm adjacent to the microscope and consequently the space to be freely utilized in operation is considerably limited. Also, each rotational axis is balanced by a balance weight, so that the balance weight has the same weight as in the microscope and the inertia force of the entire device produced when the microscope is moved will remarkably be increased. Therefore, the above device has the disadvantage that it is very difficult to stop rapidly and securely, at a desired position, the microscope which has once been moved.

In order to further satisfy the requirements stated above, a device is known, as disclosed in, for example, German Patent Laid-Open No. 3444313, that a tension coil spring whose one end portion is fixed to a disc rotatable with an arm supporting the microscope is movably mounted in a radial direction at the other end portion and rotation moment according to gravity acting on the microscope at various setting positions of the microscope is balanced with the tension of the coil spring so that the movement and stop of the microscope can smoothly be carried out. This device, however, has the defect that it is unsuitable for the support of the surgical microscope since the movement of the microscope is limited two dimensions.

SUMMARY OF THE INVENTION

Therefore, a primary object of the present invention is to provide a tilting device for surgical microscopes capable of varying the orientation or angular position of a surgical microscope under always balanced conditions and with a slight force of operation.

A further object of the present invention is to provide a tilting device for surgical microscopes capable of securing a sufficient working space for a surgical operation in spite of a comparatively small size.

Still a further object of the present invention is to provide a titting device for surgical microscopes capable of being manufactured with a simple structure and at a low cost.

According to the present invention, these objects are accomplished by providing a suporting apparatus, constructed to be rotatable about an axis and a center pivot perpendicular to each other, to be mounted on a frame or a stand through a mounting member; and a resilient member connected between the end portion of the supporting apparatus at a distance from the intersection of the center axis and the center pivot and making an arrangement so that rotation moment caused by the weight of the microscope with the rotational movement of the center of gravity of the microscope attached to another end of the supporting apparatus at a distance from the above intersection is offset by reverse rotation moment relying on the elasticity of the resilient member.

According to a preferred formation of the present invention, the supporting apparatus comprises a parallelogram link and the elastic member is composed of a tension coil spring or a compression coil spring. Thereby, the device can be manufactured with a relatively simple structure and at a low cost.

According to another preferred formation of the present invention, the entire supporting apparatus is attached to the mounting member in such a manner that its rotational axis is inclined downward by a predetermined angle with respect to a vertical arm or a vertical line, and the elastic member is coupled between a member disposed midway in a longitudinal direction of the parallelogram link mechanism for te supporting member and the mounting member. Therefore, the device can be constructed to be smaller and compact in size.

These and other objects as well as the features and the advantages of the present invention will be apparent from the following detailed description of the preferred embodiments when taken in conjunction with the accompanying drawings.

DESCRIPTION OF THE PREFERRED EMBODIMENT

First of all, referring to FIGS. 1 through 4, a first embodiment according to the present invention will be described hereinafter.

Figure 1:
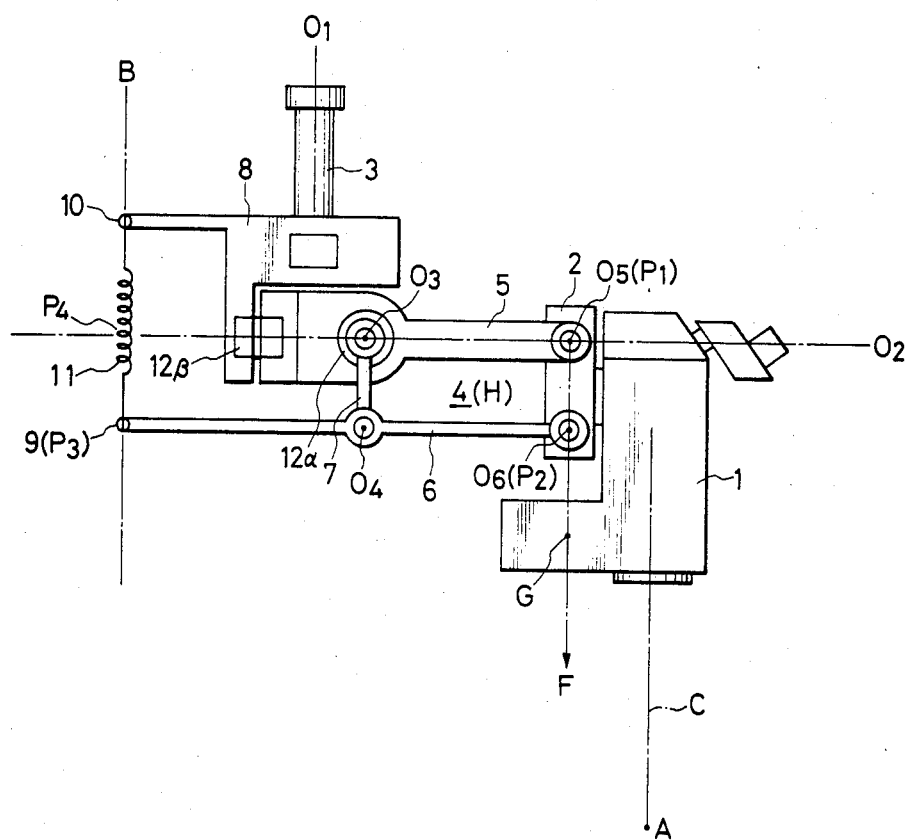
FIG. 1 is a structural view showing the principle of a first embodiment of a tilting device according to the present invention.

In FIG. 1, reference numeral 1 designates a known microscope supported to be vertically movable along an observing optical axis C through a focusing section 2. The focusing section 2 constitutes one of link arms of supporting means 4 constructed as a parallelogram linkage attached to the lower portion of a vertical arm 3 through a mounting member 8. To the focusing section 2, two horizontal link arms 5, 6 parallel to each other are rotatably connected through pivots $O_5$, $O_6$ at one ends thereof. Each other end of the horizontal link arms 5, 6 is rotatably coupled to a link 7 parallel to the vertical arm 3 through pivots $O_3$, $O_4$. The horizontal link 5 is rotatably connected to the mounting member 8 at the end in a predetermined distance from the pivot $O_5$, aligning with a center axis $O_2$ passing through the centers of the pivots $O_3$ and $O_5$. Further, the vertical arm 3 is secured to the mounting member 8, which is mounted to be freely rotatable on an axis $O_1$ perpendicular to a frame which will be described later, through the vertical arm 3. Pivots $O_3$, $O_4$, $O_5$, $O_6$ extend in a direction making right angles with the axis $O_2$. Between an extending end 9 at a distance from the pivots $O_6$, $O_4$ of the horizontal link 6 and a projecting end 10 provided on the mounting member 8, a balance spring 11 is connected in a state of initial tension. Both the extending end 9 and the projecting end 10 lie on a vertical line B when the link 7 is in a vertical position (initial state) as shown in FIG. 1. Also, weight F of the microscope 1 then applied to center of gravity G of the microscope 1 and the observing optical axis C are included in a plane H containing the parallelogram link 4 and the center of gravity G lies on a straight line connecting intersections $P_1$, $P_2$ of the plane H with the pivots $O_5$, $O_6$. However, the weight of other mechanism portions is represented by the weight F applied to the center of gravity of the microscope 1. The axes $O_1$ and $O_2$, as well as the case of the axis $O_2$ and the pivot $O_5$, are normal to each other and, when the position of the microscope 1 is shifted from the initial state within the three-dimensional space by a handle, not shown in the drawings, provided in the microscope 1, individual pivots are oriented with angles corresponding to its rotational movement to be positioned. Between the horizontal arm 5 and the pivot $O_3$ and between the mounting member 8 and the end portion of the horizontal arm 5, known electromagnetic brakes 12α, 12β are disposed respectively to fix or release the microscope 1 through the operation of a control switch, not shown, provided adjacent to the handle so that the microscope 1 can be held at and rotated into a desired position.

Figure 2:
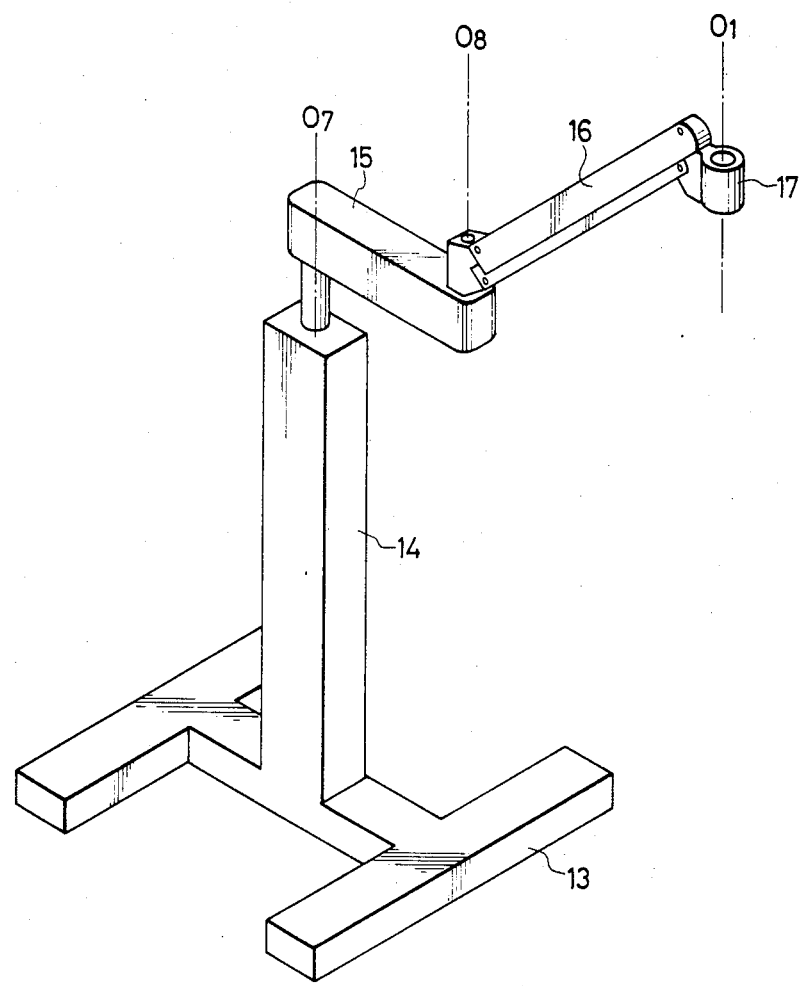
FIG. 2 is a perspective view of a frame or a stand apparatus suspending the tilting device according to the present invention.

Next, in FIG. 2, which shows the frame reference numeral 13 represents a base, 14 a post standing upright on the base 13, 15 a first arm supported to be freely rotatable about a vertical axis $O_7$ on the post 14, and 16 a second arm supported to be freely rotatable about a vertical axis $O_8$ at the other end of the first arm 15 and in a plane normal to the first arm 15. At the top portion of the second arm 16 is provided a bearing portion 17 for journaling pivotally the vertical arm 3 shown in FIG. 1. Further, in the second arm 16, a balancing mechanism for balancing a load applied to the bearing portion 17 is incorporated (not shown) and, in virtue of parallelogram link mechanism 4 mentioned above, an operator can move three-dimensionally the microscope 1 with a light force while the arm 3 is vertically held.

Next, referring to FIG. 3, the function of the above tilting device will be described below.

Figure 3:
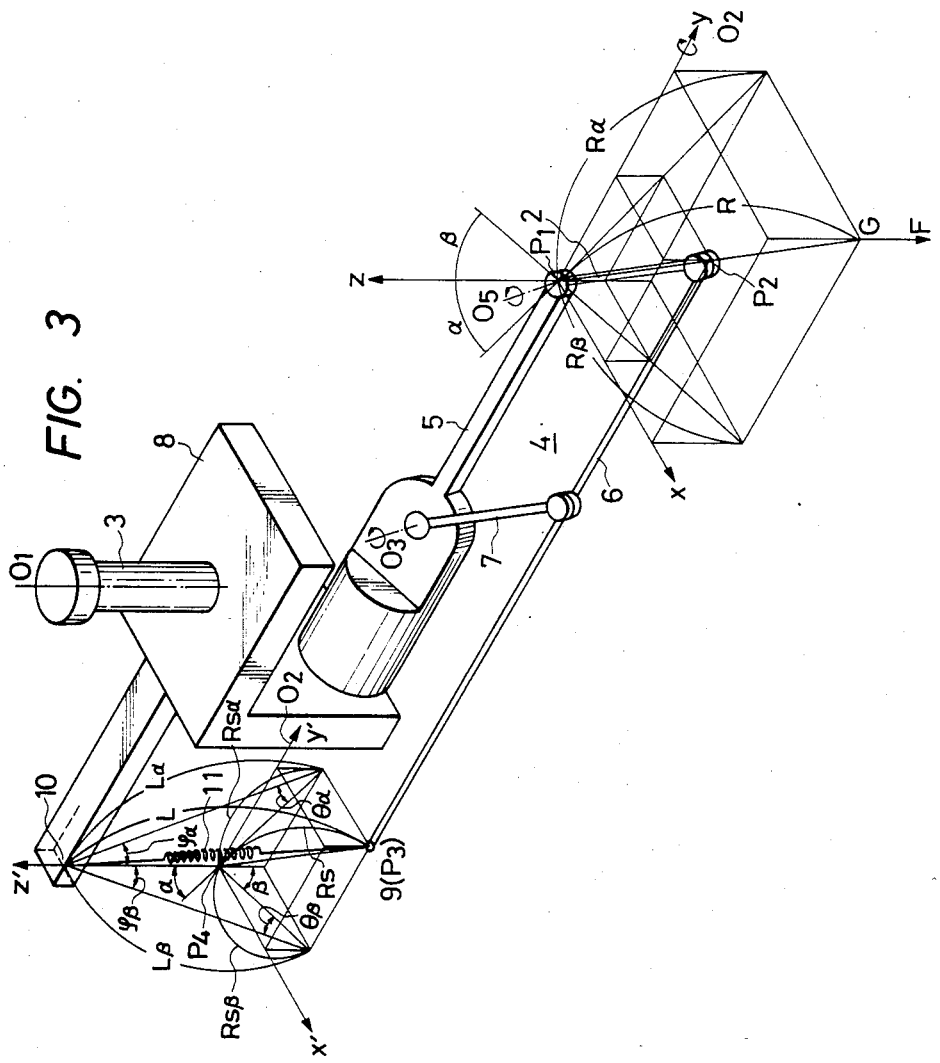
FIG. 3 is a schematic perspective view for explaining the function of the tilting device shown in FIG. 1.

FIG. 3 shows the microscope 1 as somewhat rotated around the horizontal axis $O_2$ and the center $O_5$ in the apparatus in FIG. 1.

First of all, the rotatory movement produced by the load F applied to the center of gravity G of the microscope 1 shall be explained. That is to say, when the microscope 1 is rotated around the horizontal axis $O_2$ and rotary axis $O_3$, the point $P_2$ or center of gravity G will make a spherical motion with the first center of ratation $P_1$ of the arm 5 as a rotation center. Now, if the point $P_1$ is made an origin, the axis parallel with the vertical axis $O_1$ is made a z coordinate axis, the horizontal axis $O_2$ is made a y coordinate axis and the axis vertical to the plane including the z coordinate axis and y coordinate axis is made an x coordinate axis, the above mentioned rotatory moment can be explained as decomposed into an x coordinate axis component and y coordinate axis component.

Here, if the gravity acting on the center of gravity G is represented by F, the distance from the origin $P_1$ to the center of gravity is represented by R, the rotation angle around the x axis is represented by α, the rotation angle around the y axis is represented by β, the projected image of R on the y - z plane is represented by $R_{60}$, the projected image of R on the x - z plane is represented by $R_{62}$, and the rotatory moments acting respectively on the x axis and y axis are represented respectively by $M_x$ and $M_y$, $$M_x = F \cdot R_\alpha \cdot \sin \alpha \text{ and}$$

$$M_y = F \cdot R_{62} \cdot \sin \beta$$

where $$R_\alpha = \sqrt{\frac{R^2}{1 + \cos^2\alpha \tan^2\beta}}$$

and $$R_\beta = \sqrt{\frac{R^2}{1 + \cos^2\beta \tan^2\alpha}}.$$

Figure 4:
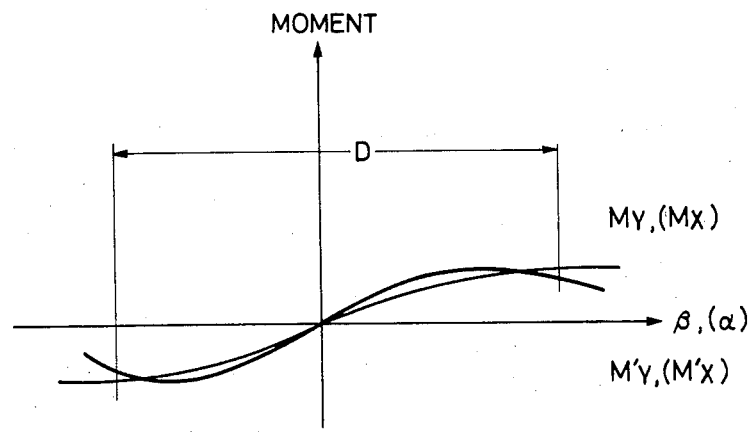
FIG. 4 is a chart showing a balance state of operation moment of the tilting device according to the present invention.

The above formulae $M_x$ and $M_y$ include respectively $\sin\alpha$ and $\sin\beta$ in the primary form. FIG. 4 shows the variation of $M_y$ (moment) in case a is constant ($\alpha=a$) but $\beta$ is continuously varied.

Now, the rotatory moment acting with the resiliency of the spring 11 on the point $P_3$ on the extension of the link 6 when the microscope 1 is moved as mentioned above shall be considered. That is to say, when the microscope 1 is rotated around the axis $O_2$ and pivot $O_5$, the extension end 9 of the horizontal link 6 will make a spherical motion with the distance $R_s$ between the intersection $P_4$ of the horizontal axis $O_2$ with the line B connecting the extension end 9 in the initial state and the projection end 10 and the extension end 9 as a radius. In this case, the same as in the above described case, if the second center of rotation $P_4$ is made an origin, the axis parallel with the vertical axis $O_1$ is made a z' coordinate axis, the horizontal axis $O_z$ is made a y' coordinate axis and the axis vertical to the plane including the z' axis and y' axis is made an x' coordinate axis, the rotatory moment acting on the point $P_3$ with the resiliency of the spring 11 can be considered to be a compound of the rotatory moments acting respectively on the x' axis and y' axis.

Here, if the resiliency of the spring 7 is represented by $F_s$, the distance from the origin $P_4$ to the tip 9 of the horizontal link 6 is represented by $R_s$, the rotation angle with respect to the x' axis is represented by $\alpha$, the rotation angle with respect to the y' axis is represented by $\beta$, the length of the spring is represented by L, the projected image of $R_s$ on the y'-z' plane is represented by $R_{s\alpha}$, the projected image of $R_s$ on the x'-z' plane is represented by $R_{s\beta}$, the projected image of L on the y'-z' plane is represented by $L_\alpha$, the projected image of L on the x'-z' plane is represented by $L_\beta$, the angle made by $L_\alpha$ with $R_{s\alpha}$ is represented by $\theta_\alpha$, the angle made by $L_\beta$ with $R_{s\beta}$ is represented by $\theta_\beta$, the distance from the origin $P_4$ to the projection end 10 of the fitting member 8 is represented by Z and the rotatory moments with respect to the x' axis and y' axis by the resiliency $F_s$ of the spring 11 are represented respectively by $M_x'$ and $M_y'$, $$M_x' = F_s \cdot R_{s\alpha} \cdot \sin\theta_\alpha$$

$$M_y' = F_s \cdot R_{s\beta} \cdot \sin\theta_\beta$$

where $$F_s = K(L - L_o) + P_o$$

($F_s$ is positive (+) with a compression spring but negative (−) with a tension spring.) where K represents a spring constant of the spring 11,
$L_o$ represents a free length of the spring 11 and
$P_o$ represents an initial tension of the spring 11, $$R_{s\alpha} = \sqrt{\frac{R_s^2}{1 + \cos^2\alpha \tan^2\beta}}$$

$$R_{s\beta} = \sqrt{\frac{R_s^2}{1 + \cos^2\beta \tan^2\alpha}}$$

$$L = \sqrt{Z^2 + 2ZR_{s\alpha}\cos\alpha + R_s^2}$$

$$\theta_\alpha = \alpha - \tan^{-1}\left(\frac{R_{s\alpha}\sin\alpha}{Z + R_{s\alpha}\cos\alpha}\right)$$

$$\theta_\beta = \beta - \tan^{-1}\left(\frac{R_{s\beta}\sin\beta}{Z + R_{s\beta}\cos\beta}\right)$$

The above formulae $M_x''0$ and $M_y''$, too, include respectively $\sin\theta_\alpha$ and $\sin\theta_\beta$ in the primary form. Also, when $\theta$ is $\alpha \to 0$ or $\beta \to 0$, $\theta \to \alpha$ or $\theta \to \beta$.

FIG. 4 shows the variation of $M_y'$ in case the variable $\theta$ is replaced with the variable $\beta$ in parallel with a curve showing the variation of $M_y$ (moment) by the center of gravity in case $\beta$ is varied when $\alpha=a$. The same curve can be shown also on $M_x$ and $M_x'$.

In all the adjusting processes wherein the microscope 1 is tilted and rotated, the rotatory moments as balanced are realized by being $M_x + M_x' = 0$ and $M_y + M_y' = 0$. That is to say, with respect to the x(x') axis and y(y') axis, the rotatory moment by the weight of the movable part of the apparatus and the rotatory moment by the resiliency of the spring may be balanced with each other. Here, if the conditions are properly determined, $M_x$ and $M_x'$ and $M_y$ and $M_y'$ can be simultaneously respectively balanced with each other as shown in FIG. 4 over a range D with respect to any rotation angles $\alpha$ and $\beta$. FIG. 4 shows $M_x$ and $M_x'$ or $m_y$ and $M_y'$ as balanced with each other in case $\alpha=a$ is constant but 8 is continuously varied. Here, for the sake of comparison, $M_x'$ and $M_y'$ are indicated with the signs reversed As understood from this graph, a very favorable balance is realized in a certain range. For a little unbalance, a frictional force is made to act in the rotating direction of the axis during the use but, as the balancing force by the spring acts, the minimum frictional force may be applied. Therefore, the microscope 11 can be operated to be elevated with a very light force.

The operating method of the above-mentioned tilting device shall be explained in the following. First of all, when the microscope 1 is to be moved, a switch provided on a handle not illustrated fitted to the microscope 1 is operated to release the braking action of the electromagnetic brakes 12 and 12 . Thereby, the microscope is adjusted to take any desired inclined posture in a three-dimensional free position as suspended over the mounting base 13 through the arms 15 and 16, fitting member 8 and supporting means 4. Such adjusting operation can be very lightly made, because no deflected force will act on the respective rotary shaft parts due to the balance of the rotatory moment by the weight of the microscope 1 and the reverse rotatory moment by the balance spring 11. Also, the inertia mass is so small as different from the conventional apparatus using a weight for balancing that it is easy to stop the microscope in any desired position Thus, when the microscope 1 has been brought in any desired inclined posture to any desired position, if the above-mentioned switch is operated again to actuate the electromagnetic brakes 12α and 12β, the microscope 1 can be held in that state.

Figure 5:
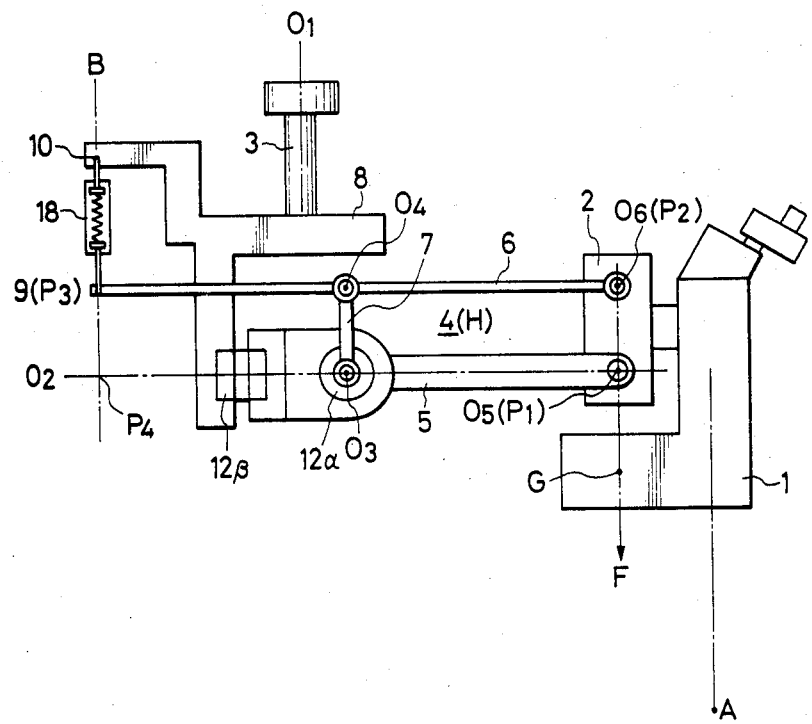
FIG. 5 is a structural view showing the principle of a second embodiment of the tilting device according to the present invention.

FIG. 5 shows the second embodiment of the tilting device by the invention of the present application. The same reference numerals are attached to the component parts and portions similar to those of the above described first embodiment. A compression coil spring 18 is used instead of the tension coil spring 11. That is to say, as illustrated, this second embodiment is different from the first embodiment in respect that, as the link 7 is located on the side reverse to the center of gravity G with respect to the axis $O_2$, the compression coil spring 18 is used but the other formations and operations are the same as in the case of the first embodiment and therefore no detailed explanation shall be made.

Figure 6:
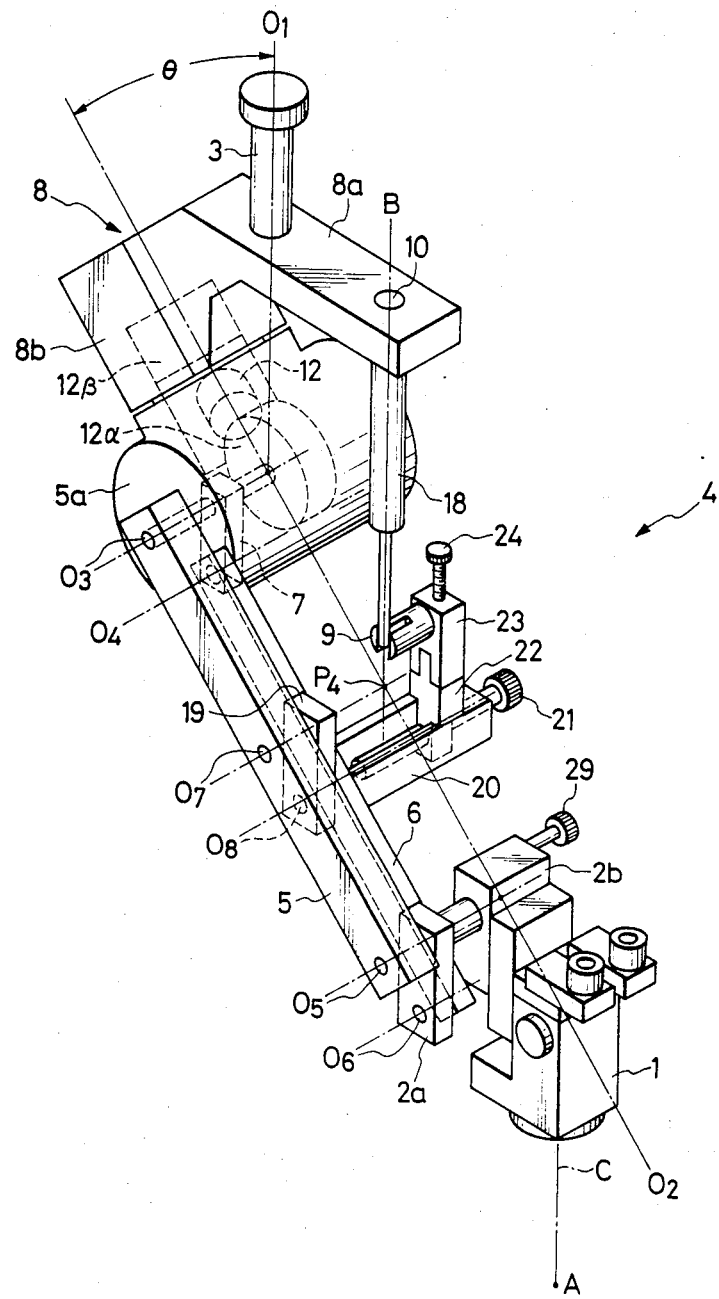
FIG. 6 is a perspective view showing an essential portion of a third embodiment of the tilting device according to the present invention.
Figure 7:
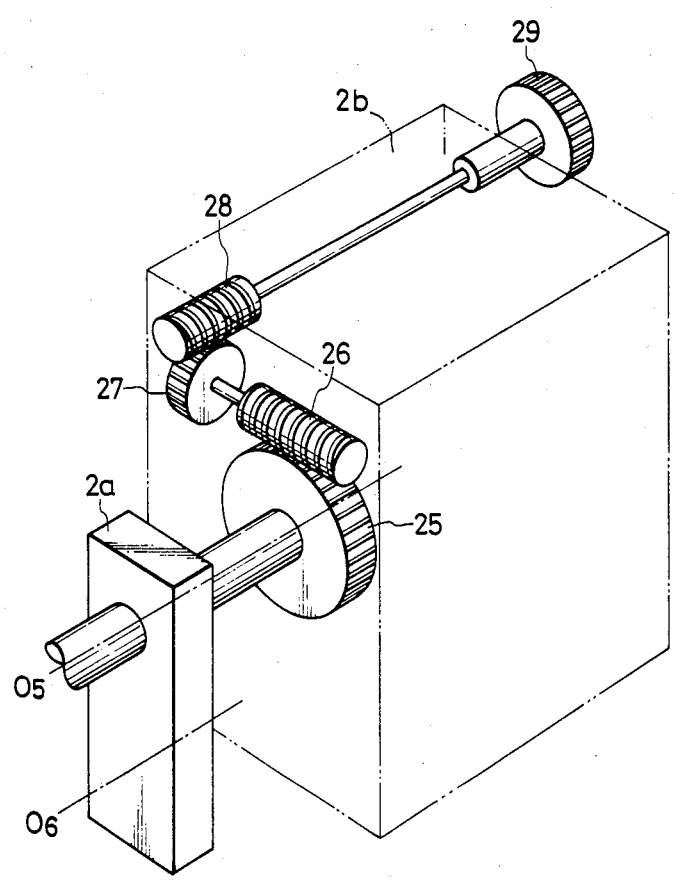
FIG. 7 is an enlarged perspective view of a focusing section of a microscope attached to the tilting device according to the present invention.

FIGS. 6 and 7 show a third embodiment of the tilting device according to the present invention. Also in this embodiment, like reference numerals are used to designate like parts and portions employed in the embodiments which have already been described. The third embodiment is different from the other embodiments in that the center line or the center axis $O_2$ extending in a longitudinal direction of the supporting means 4 is provided to tilt downward in such a manner that it makes a predetermined angle $\theta$ with the axis $O_1$ of the vertical arm 3 or the vertical line; that the compression spring 18 is disposed at an intermediate point of the supporting apparatus 4 to enable a connection 9 between the supporting apparatus 4 and the spring 18 to be finely preadjusted; and that an arm 2a and a focusing section 2b are not constructed integral with each other, but to be finely adjustable for previous change of a relative position. That is, the mounting member 8 is arranged so that a projecting arm section 8a having a top surface normal to the vertical arm 3 makes an angle $\theta$ with an arm section 8b holding rotatably the supporting apparatus 4. The end portion of the link arm 5 attached to the mounting member 8 is formed as a hollow cylindrical body 5a into which the link arm 7 pivotably mounted to the link arm 6 at its one end portion is inserted. The pivot $O_3$ pivoted by the link arm 5 to be rotatable is secured at the other end portion of the link arm 7 so that it is held in a stationary condition, as necessary, by the electromagnetic brake 12α fixed to the inside of the cylindrical body 5a. Further, in the cylindrical body 5a, a shaft 12 aligned with the axis $O_2$ is provided. The shaft 12 is supported rotatably to the arm section 8b of the mounting member 8 so that it is held in a stationary condition, as necessary, by the electromagnetic brake 12β provided inside the mounting member 8. In the center portion of the link arms 5, 6 is provided an intermediate link arm 19 pivotably mounted to the link arms 5, 6 in parallel with and in the same manner as in the link arms 2a, 7. Also, a pivot $O_8$ connecting the intermediate link 19 and the link arm 6 is secured to the intermediate link 19 at its one end portion and supported rotatably to the link arm 6. The other end portion of the pivot $O_8$ then extends inward and a long supporting member 20 extending in the same direction is secured therein. That is, the supporting member 20 is coupled integral with the intermediate link 19. In the supporting member 20 is supported rotatably a screw 21 extending in a longitudinal direction thereof with which a post 22 supported slidably by the supporting member 20 is threadedly engaged. Therefore, when the screw 21 is turned, the post 22 can be moved along the longitudinal direction of the supporting member 20. Another post 23 is mounted on the post 22 to be slidable in a vertical direction and a screw 24 is threadedly engaged with the post 23 in such a way that it passes vertically through the post 23. The lower end portion of the screw 24 is supported rotatably to the post 22. Therefore, when the screw 24 is turned, the post 23 can vertically be moved while being guided by the post 22. The top of the post 23 serves as the extension end 9 of the link arm 6 in the second embodiment shown in FIG. 5. In such a case, the compression spring 18 comprises a gas spring and is connected between the extension end 9 of the link arm 6 and the projecting end 10 of the mounting member 8, in principle, as in the other embodiments. The one end portion of the center pivot $O_5$ secured to the link arm 2a is rotatably supported to the link arm 5 and thereby the link arm 2a is associated with the link arm 5. The other end portion of the pivot $O_5$ is rotatably supported to the side wall of the focusing section 2b, and a worm wheel 25 is fixed to the end portion of the pivot $O_5$ projecting into the focusing section 2b. In the inside of the focusing section 2b, a worm wheel 27 constructed integral with a worm 26 which is meshed with the worm wheel 25 is rotatably supported and further, a worm 28 meshed with the worm wheel 27 is rotatably supported. A handle 29 is secured to the end portion of a rotary shaft of the worm 28 projecting from the focusing section 2b. Therefore, although the link arm 2a is usually operated integral with the focusing section 2b, when the handle is turned, its rotation is transmitted to the worm wheel 25. It follows from this that the focusing section 2b is rotated about the pivot $O_5$ only for an angle corresponding to the rotated angle of the worm wheel 25. This means that, by turning the handle 29, the microscope 1 can be moved to shift the position of the center of gravity G.

Other structures and functions of the third embodiment are the same as in the embodiments which have already been described, so that more detailed explanation is omitted. According to this embodiment, even if the position of the center of gravity G is shifted out of a regular position (shown in FIG. 3) by attaching various accessories mentioned above to the microscope 1, it can easily be brought into the regular position by turning the screws 21, 24 and/or the handle 29. Further, it is possible to make fine adjustment so that the relationship shown in FIG. 3 can be held and to hold always the best balance, by operating the screws 21, 24 and/or the handle 29.

What is claimed is:

1. A tilting device for surgical microscopes comprising:
   a mounting member suspended to be movable three-dimensionally on a frame;
   a supporting means coupled to said mounting member and having a first center of rotation arranged to be rotatable about a center axis and a center pivot perpendicular to each other and having one end portion capable of mounting a microscope; and
   a resilient member connected between said mounting member and the other end portion of said supporting means, whereby rotation moment caused by the weight of the microscope with rotational movement of the center of gravity of the microscope through said supporting means is offset by reverse rotation movement relying on the elasticity of said resilient member.

2. A tilting device according to claim 1, wherein:

said supporting means has a second center of rotation which is an intersection of said center axis with a vertical line passing through a connection between said mounting member and said resilient member, and is arranged to be rotatable about said second center of rotation in accordance with the rotation of said supporting means about said first center of rotation.

3. A tilting device according to claim 2, wherein:

a line segment connecting the center of gravity of the microscope attached to said supporting means with said first center of rotation is parallel to a segment connecting a connection between said supporting means and said resilient member with said second center of rotation., 4. A tilting device according to claim 2, wherein:

said supporting means is mounted on said frame through said mounting member at a position distant from said first and second centers of rotation.

5. A tilting device according to claim 2, wherein:

said supporting means is attached to said mounting member so that the axis connecting said first center of rotation and said second center of rotation is inclined downward, and said second center of rotation is provided adjacent to the vertical line passing through the connection between said mounting member and said resilient member.

6. A tilting device according to claim 1, wherein:

said supporting means comprises a parallelogram linkage having a pair of link arms parallel to said center axis.

7. A tilting device according to claim 6, wherein:

said supporting means further comprises an intermediate link arm pivotably mounted to respective intermediate portions of said pair of link arms and a supporting device capable of moving integral with said intermediate link arm; and said resilient member is connected between said mounting member and said supporting device.

8. A tilting device according to claim 7, wherein:

said supporting device is constructed to be movable in an axial direction of a pivot of said intermediate link arm.

9. A tilting device according to claim 7 or 8, wherein:

said supporting device is further constructed to be movable in a direction normal to an axis of the pivot of said intermediate link arm.

10. A tilting device according to claim 6, wherein:

the microscope is attached to a link arm pivotably mounted to each one end portion of said pair of link arms so that a relative position of the microscope to said link arm can be preadjusted.

11. A tilting device according to claim 1, wherein:

said supporting means is coupled to said mounting member through a constraining means capable of constraining a relative movement of said supporting means and said mounting means.

12. A tilting device according to claim 6, wherein:

a constraining means capable of constraining pivotal movement of said parallelogram link is provided in any one of pivots of respective link arms constituting said parallelogram link.

13. A tilting device according to claim 11 or 12, wherein:

said constraining means is a brake device capable of being operated by remote control.

* * * * *